US007919256B2

(12) United States Patent
Yamaguchi et al.

(10) Patent No.: US 7,919,256 B2
(45) Date of Patent: Apr. 5, 2011

(54) METHOD FOR DETECTING BORNA DISEASE VIRUS INFECTION

(75) Inventors: Kazunari Yamaguchi, Musashimurayama (JP); Yoichiro Horii, Miyazaki (JP); Youichi Takahama, Kobe (JP); Shinya Nagai, Kobe (JP)

(73) Assignee: Sysmex Corporation, Hyogo (JP)

( * ) Notice: Subject to any disclaimer, the term of this patent is extended or adjusted under 35 U.S.C. 154(b) by 510 days.

(21) Appl. No.: 10/805,220

(22) Filed: Mar. 22, 2004

(65) Prior Publication Data

US 2004/0234955 A1 Nov. 25, 2004

(30) Foreign Application Priority Data

Mar. 20, 2003 (JP) ................. 2003-078898
Mar. 26, 2003 (JP) ................. 2003-086490
Mar. 26, 2003 (JP) ................. 2003-086491

(51) Int. Cl.
*G01N 33/53* (2006.01)

(52) U.S. Cl. ................... 435/7.1; 424/159.1; 424/186.1; 424/204.1

(58) Field of Classification Search ............... 424/211.1, 424/159.1; 435/5
See application file for complete search history.

(56) References Cited

U.S. PATENT DOCUMENTS

| 6,074,817 | A | 6/2000 | Landini et al. |
| 6,077,510 | A | 6/2000 | Lipkin et al. |
| 6,403,301 | B1 | 6/2002 | Ludwig et al. |

FOREIGN PATENT DOCUMENTS

| EP | 0 791 654 A1 | 8/1997 |
| JP | 11-180998 A | 7/1999 |
| WO | WO 96/21020 A2 | 7/1996 |

OTHER PUBLICATIONS

Yamaguchi et al. Annals of Clinical Biochemistry, Jul. 2001, vol. 38, pp. 348-355.*
Carbone, Kathryn M. Borna Disease Virus and Human Disease, Clinical Microbiology Reviews, Jul. 2001, 14(3):513-527.*
Hatalski et al. Neutralizing Antibodies in Borna Disease Virus-Infected Rats, Journal of Virology, Feb. 1995, 69(2):741-747.*
Rinsho Kensaho Teiyou (Guidebook on laboratory test), Kabegara & Co., Ltd. 31$^{st}$ Edition, 1998, p. 818-820).
(Guidebook on laboratory test) Kanehehara & Co., Ltd., 31$^{st}$ Edition, 1998, p. 807-809.
Narayan et al. *Science* 220:1401-1402 (1993).
Pauli et al. *Zbl. Vet. Med. B*. 31:552-557 (1984).
Inoue et al. *J. Vet. Med. Sci*. 64(5):445-448 (2002).
Rybakowski et al. *Med. Sci. Monit*. 8(9):CR642-646 (2002).
M. Wantanabe et al., Antibodies To Borna Disease Virus In Infected Adult Rats: An Early Appearance Of Anti-p10 Antibody And Recognition Of Novel Virus-Specific Proteins In Infected Animal Brain Cells, The Journal of Veterinary Medical Science/The Japanese Society of Veterinary Science, Jul. 2000, pp. 775-778, vol. 62—No. 7.
T. Briese et al., Enzyme-Linked Immunosorbent Assay For Detecting Antibodies To Bornadisease Virus-Specific Proteins, Journal of Clinical Microbiology, Feb. 1, 1995, pp. 348-351, vol. 33—No. 2.
Z. Rosenzweig et al, Laser-Based Particle-Couting Microimmunoassay For The Analysis Of Single Human Erythrocytes, Analytical Chemistry, American Chemical Society, May 15, 1994, pp. 1771-1776, vol. 66—No. 10.
Norbert Nowotny et al., Isolation And Characterization Of A New Subtype Of Borna Disease Virus, Journal of Virology, Jun. 2000, pp. 5655-5658, vol. 74—No. 12.
O. Planz et al., Pathogenesis Of Borna Disease Virus: Granulocyte Fractions Of Psychiatric Patients Harbor Infectious Virus In The Absence Of Antiviral Antibodies, Journal of Virology, Aug. 1999, pp. 6251-6256, vol. 73—No. 8.
H. Ludwig et al., Borna Disease A Persistent Virus Infection Of The Central Nervous System, Progress in Medical Virology, 1998, pp. 107-151, vol. 35.

* cited by examiner

*Primary Examiner* — Stacy B Chen
(74) *Attorney, Agent, or Firm* — Sughrue Mion, PLLC

(57) ABSTRACT

A method for the early detection of disease through the use of reagents bound by IgM antibodies is described. A reagent and method for the detection of anti-Borna disease virus antibodies are also described.

3 Claims, 9 Drawing Sheets

```
SEQUENCE LISTING

<160> NUMBER OF SEQ ID NOS: 8

<210> SEQ ID NO 1
<211> LENGTH: 15
<212> TYPE: PRT
<213> ORGANISM: Borna disease virus

<400> SEQUENCE: 1

Gln Pro Val Asp Gln Leu Leu Lys Asp Leu Arg Lys Asn Pro Ser
1               5                   10                  15

<210> SEQ ID NO 2
<211> LENGTH: 17
<212> TYPE: PRT
<213> ORGANISM: Borna disease virus

<400> SEQUENCE: 2

Asp Pro Asp Gln Arg Thr Gly Arg Glu Gln Leu Ser Asn Asp Glu Leu
1               5                   10                  15

Ile

<210> SEQ ID NO 3
<211> LENGTH: 18
<212> TYPE: PRT
<213> ORGANISM: Borna disease virus

<400> SEQUENCE: 3

Pro Lys Arg Arg Leu Val Asp Asp Ala Asp Ala Met Glu Asp Gln Asp
1               5                   10                  15

Leu Tyr

<210> SEQ ID NO 4
```

```
<211> LENGTH: 19
<212> TYPE: PRT
<213> ORGANISM: Borna disease virus

<400> SEQUENCE: 4

Arg Tyr Arg Arg Arg Glu Ile Ser Arg Gly Glu Asp Gly Ala Glu Leu
1               5                   10                  15

Ser Gly Glu

<210> SEQ ID NO 5
<211> LENGTH: 19
<212> TYPE: PRT
<213> ORGANISM: Borna disease virus

<400> SEQUENCE: 5

Gly Asn Thr Thr Val Glu Ser Gly Arg Leu Ser Gly Gly Arg Arg Arg
1               5                   10                  15

Ser Pro Asp

<210> SEQ ID NO 6
<211> LENGTH: 15
<212> TYPE: PRT
<213> ORGANISM: Borna disease virus

<400> SEQUENCE: 6

Gly Leu Thr Lys Thr Lys Glu Asp Ser Lys Glu Cys Thr Asp Pro
1               5                   10                  15

<210> SEQ ID NO 7
<211> LENGTH: 19
<212> TYPE: PRT
<213> ORGANISM: Borna disease virus

<400> SEQUENCE: 7

Gly Asn Ala Thr Ile Glu Ser Gly Arg Leu Pro Gly Gly Arg Arg Arg
1               5                   10                  15

Ser Pro Asp

<210> SEQ ID NO 8
<211> LENGTH: 15
<212> TYPE: PRT
<213> ORGANISM: Borna disease virus

<400> SEQUENCE: 8

Gly Val Thr Lys Thr Thr Glu Asp Pro Lys Glu Cys Thr Asp Pro
1               5                   10                  15
```

METHOD FOR DETECTING BORNA DISEASE VIRUS INFECTION

FIELD OF THE INVENTION

The present invention relates to a method for detecting an antibody to a exogenous antigen such as Borna disease virus or the like, and an antigen for detecting Borna disease virus.

BACKGROUND ART

There exists each class of immunoglobulins such as IgG, IgA, IgM, IgD and IgE. IgM antibodies are first raised in response to the stimulation of an antigen, and rapidly disappear owing to the short half life thereof. Thus, they are gradually replaced with IgG. Allogenic hemagglutinin, rheumatoid factors, heterophile antibodies and cold agglutinin predominantly belong to this IgM (Rinsho Kensaho Teiyou (Guidebook on laboratory test), Kanehara & Co., Ltd., 31st. Edition, 1998, p. 820).

In cases of infectious diseases, it is diagnostically useful to measure both specific antibody titers of the serum in the initial stage of the infection and of the serum in the stage convalescent, pairwise (Guidebook on laboratory test), Kanehara & Co., Ltd., 31st. Edition, 1998, p. 808). For example, a method for detecting IgM has been reported for the purpose of determining the infection with human cytomegalovirus (HCMV) (Japanese Translation Provisional Publication No. Hei10-502253). However, there has not been disclosed any method for concurrently detecting IgG and IgM.

Class switching from IgM to IgG of immunoglobulins has been generally known to be achieved within approximately one month following the appearance of the IgM. However, many of the natures of candidate substances which may be an antigen have been unknown, and a period of time required for the class switching of an immunoglobulin as well as other characteristics have not yet been elucidated in many aspects.

For example, in connection with Borna disease which is an immune related neurologic syndrome of which causative virus is Borna disease virus (hereinafter, referred to as "BDV"), many matters have not been elucidated yet. Borna disease is a viral encephalomyelitis caused in a horse through the four seasons in Germany as well as surrounding nations thereof. It exhibits symptoms such as cerebral palsy, affective disorder and the like, which may be lethal when it follows the acute process. When a rat is experimentally infected with this virus, a polyphasic syndrome characterized by hyperkinesia, stereotyped behavior, dyskinesia and ataxia is developed (O. Narayan et al., Science, 220:1401-1403 (1983)).

BDV has been known of its pathogenicity toward horses that are the natural hosts thereof, and the existence of an antibody that reacts with BDV was indicated in the serum of a patient suffering from a mental disorder in 1985, suggesting the probability of pathogenesis also toward humans. Infectious epidemiologic studies of BDV shall greatly contribute to understandings of the mental disorders. Recently, a BDV gene has been found in hemocytes including gene clusters of mental disorders with a certain frequency.

Because BDV proliferates at just a low titer, purification for executing an analysis is difficult. Diagnoses of BDV infection have been carried out through detecting the appearance of clinical symptoms that are common in this disease, and detecting a serum antibody that detects a viral protein in an infected cell by an indirect immunofluorescence technique (IFT) (G. Pauli et al., Zbl. Vet. Med. [B], 31: 552-557 (1984)), Western blot, immunoprecipitation or the like. Operation in these methods is complicated, therefore, it is difficult to use those in a mass investigation of a group of humans or livestocks.

The sequence of BDV has been already elucidated, and a method for detecting an anti-BDV antibody by an ELISA method has been reported, where p23, recp23, p40 and recp40 antigens are used (Japanese Patent Provisional Publication No. 2001-190288). In addition, a test method involving the determination of a BDV specific circulating immune complex (CIC) in plasma was also reported, where p40 and p24 antigens have been used (Japanese Translation Provisional Publication No. 2002-500363). Moreover, a method for detecting an antibody by magnetic beads in which an antigen polypeptide including a specific amino acid sequence selected from p40 and p24 regions was also reported (Japanese Patent Provisional Publication No. Hei11-180998)

However, characteristic features of BDV have been still far from being sufficiently elucidated, and many points remain unknown in connection with the period when an antibody to BDV is raised or with the accurate method for detecting an antibody. Accordingly, development of more accurate method for detecting an antibody has been desired.

An object of the present invention is to provide a reagent for detecting an anti-BDV antibody for more accurately carrying out the examination of an antibody to a exogenous antigen, particularly BDV, and to provide a method for detecting an anti-BDV antibody in which the reagent is used.

DISCLOSURE OF THE INVENTION

The present inventors elaborately investigated in order to achieve the problems as described above, and focused attention to the existence of immunoglobulins, which are raised against a exogenous antigen, that may often necessitate two months or longer, more specifically, one year or longer for the class switching from IgM to IgG. Accordingly, the method for detecting an antibody of the present invention was accomplished. In addition, the present inventors found that the aforementioned problems can be solved through using an antigen selected from the p10 region alone, or in combination with an antigen polypeptide selected from the p24 region and/or p40 region, among the proteins that constitute BDV. Thus, the reagent for detecting an anti-BDV antibody of the present invention was accomplished.

Accordingly, the present invention is directed to:

1) A method for detecting an antibody wherein an examination of a disease caused by an exogenous antigen is conducted, said exogenous antigen being an antigen having a property in which the class switching from the IgM antibody to the IgG antibody of immunoglobulin antibodies raised against said antigen is achieved after two months following the appearance of the IgM antibody, said method comprising detecting the IgM antibody to said exogenous antigen;

2) The method for detecting an antibody according to the above item 1) wherein the detection of the antibody to said exogenous antigen is carried out by detecting the IgM antibody alone, or concurrently detecting the IgM antibody and IgG antibody;

3) The method for detecting an antibody according to the above item 1) wherein said exogenous antigen is a microorganism, virus and/or proteinous substance which may be the cause of a disease of a human or of a mammal other than humans;

4) The method for detecting an antibody according to the above item 1) wherein said exogenous antigen is Borna disease virus (BDV);

5) A method for detecting an antibody wherein an examination of a disease caused by Borna disease virus (BDV) is conducted,
said method comprising detecting the IgM antibody alone, or concurrently detecting the IgM antibody and IgG antibody which is (are) raised against the virus;

6) The method for detecting an antibody according to the above item 1) wherein said method for detecting an antibody is an immune agglutination reaction method;

7) The method for detecting an antibody according to the above item 6) wherein said immune agglutination reaction method is a fine particle counting immunoassay method;

8) A reagent for detecting an anti-BDV antibody which has an antigen polypeptide selected from the p10 region of a Borna disease virus (BDV) protein;

9) The reagent for detecting an anti-BDV antibody wherein the antigen polypeptide according to the above item 8) comprises an antigen polypeptide has at least 8 amino acids;

10) The reagent for detecting an anti-BDV antibody wherein the antigen polypeptide according to the above item 8) has a polypeptide which includes an amino acid sequence set out in SEQ ID NO: 5, 6, 7 or 8;

11) A method for detecting an anti-BDV antibody wherein the antigen polypeptide according to the above item 8) is used;

12) A method for detecting an anti-BDV antibody wherein the antigen polypeptide according to the above item 8), and an antigen polypeptide selected from the p24 region and/or p40 region of a Borna disease virus (BDV) protein are used;

13) The method for detecting an anti-BDV antibody wherein the antigen polypeptide from the p24 region according to the above item 12) has a polypeptide including an amino acid sequence set out in SEQ ID NO: 1 or 2;

14) The method for detecting an anti-BDV antibody wherein the antigen polypeptide from the p40 region according to the above item 12) has a polypeptide including an amino acid sequence set out in SEQ ID NO: 3 or 4;

15) The method for detecting an anti-BDV antibody according to the above item 11) wherein said method for detecting an anti-BDV antibody is an immune agglutination reaction method; and 16) The method for detecting an antibody according to the above item 15) wherein said immune agglutination reaction method is a fine particle counting immunoassay method.

BEST MODE FOR CARRYING OUT THE INVENTION

Figure 1:
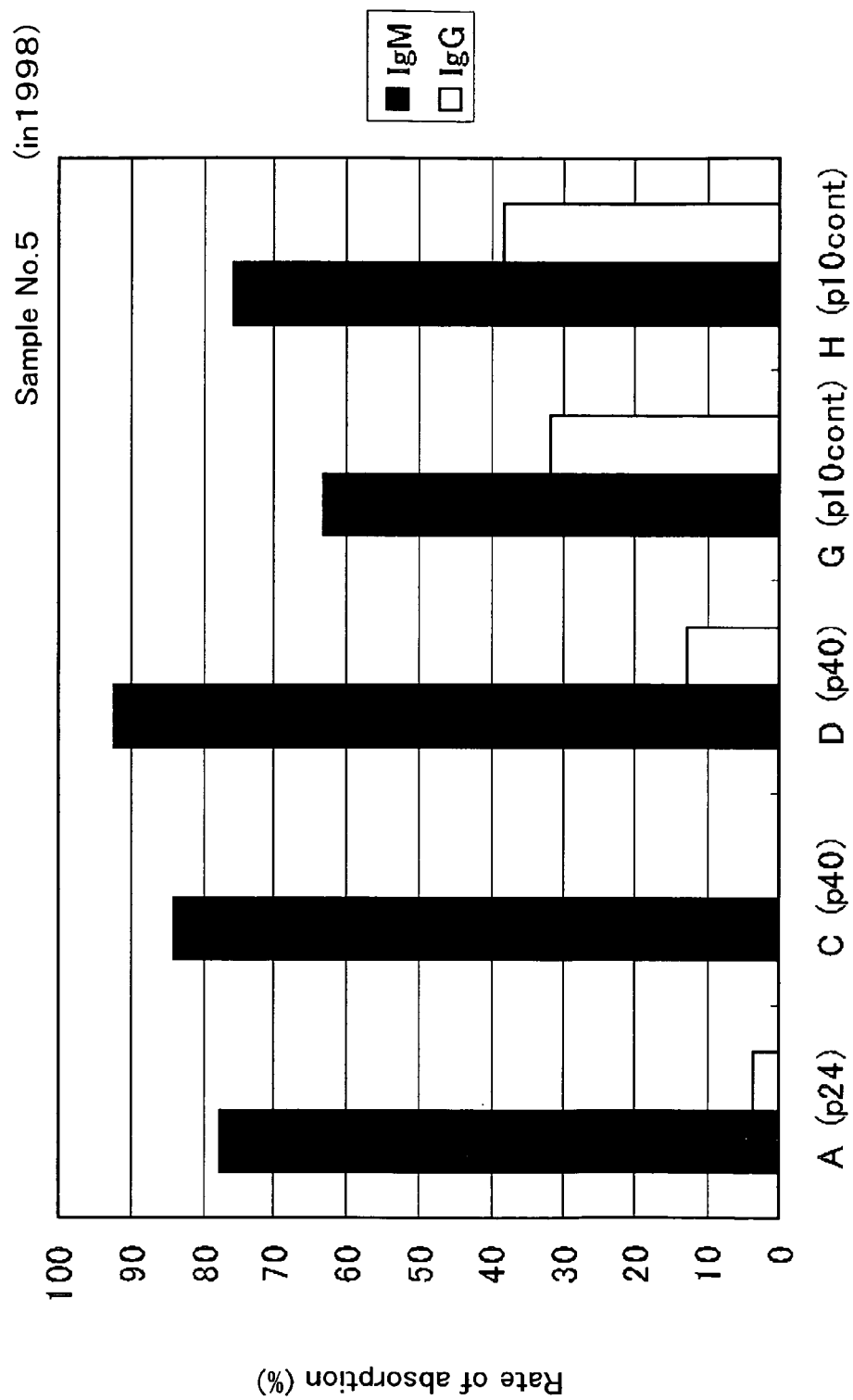
FIG. 1 A drawing showing results of the detection of a sample collected in 1998 of specimen No. 5 (Experimental Example 1).

Upon infection with a virus or the like that is an exogenous antigen, IgM first is raised, then an IgG antibody is raised while gradual decrease of the amount of the IgM. Usually, it is after 2 to 4 weeks passed following the infection when the IgG is raised, therefore, examination of the infection with a virus or the like is carried out with targeting to IgG, in general. However, the fact that a period of time required for the class switching from IgM to IgG varies depending upon the nature of the antigen has been scarcely reported heretofore. As a consequence of the study of a certain type of viruses, particularly, a slight amount of viruses, the present inventors found cases in which the class switching from IgM to IgG requires one year or longer. In such instances, it is probable that early stages of viral infections are overlooked when IgG alone is measured. Thus, the present inventors investigated method for carrying out the examination of a disease caused by an exogenous antigen in a more accurate manner, which enables the measurement of an antibody also in the early stage of the infection, in which the IgM is detected.

(Exogenous Antigen)

According to the present invention, the exogenous antigen refers to a substance that is not a component in a self living body and to an antigen that invades from outside the living body. It should be distinguished from endogenous antigens which occur due to a tissue of the self living body as in the case of autoimmune diseases. Examples of such antigens may be substances which may be the cause of a kind of a disease through invading from the external body without particular limitation, but for example, they include microorganisms such as bacteria, fungi and the like, viruses and antigenic substances such as proteins.

Specific examples of the exogenous antigen to which the method for detecting an antibody according to the present invention may be applied include some types of viruses. For example, when the amount of the infected virus is slight, and thus isolation of the virus from the living body is difficult, direct measurement of the viral component is also difficult. Therefore, examination of the infection with the virus is difficult except for by determining the appearance of the antibody to the virus. Examples of such viruses include BDV belonging to order Mononegavirales that infects nerve cells and requires a long period of time for the class switching from IgM to IgG.

On the other hand, illustrative examples of the virus that infects nerve cells, followed by embedding of the virus itself into the nerve cells, with the occurrence of the class switching from IgM to IgG in a short period of time include e.g., viruses belonging to family Herpesviridae, family Papovaviridae, family Retroviridae as well as measles virus. Viruses belonging to family Herpesviridae are classified into subfamily Alphaherpesvirinae, subfamily Betaherpesvirinae, subfamily Gammaherpesvirinae and the like. Specifically, viruses as presented below are involved.

Family Herpesviridae
  Subfamily Alphaherpesvirinae
    Genus *Simplexvirus*
      B virus=simian herpesvirus,
      Bovine thelitis virus=bovine herpesvirus,
      Herpes simplex virus 1, 2=human herpesvirus 1, 2
    Genus *Varicellovirus*
      Aujeszky virus=porcine herpesvirus 1
      Infectious bovine rhinotracheitis virus (IBR virus)=bovine herpesvirus 1
      Equine abortion herpesvirus=equine herpesvirus 1
      Herpes zoster virus=human herpesvirus 3
    Others
      Feline viral rhinotracheitis virus=feline herpesvirus 1
      Canine trachea bronchitis virus=canine herpesvirus
      Infectious laryngotracheitis virus=avian herpesvirus 1
      Duck plague virus=duck herpesvirus 1
      Bovine encephalitis herpesvirus=bovine herpesvirus 5
      Coital exanthema virus=equine herpesvirus 3
  Subfamily Betaherpesvirinae
    Genus *Cytomegalovirus*
    Genus *Roseolovirus*
      Human herpesvirus 6
    Others
      Porcine herpesvirus 2
      Equine herpesvirus 2
      Equine herpesvirus 5
      Equine herpesvirus 7
  Subfamily Gammaherpesvirinae
    Genus *Lymphocryptovirus*
      Epstein-Barr virus=human herpesvirus 4
      Chimpanzee herpesvirus
      Baboon herpesvirus
Family Papovaviridae
  Genus *Polyomavirus*
    Simian renal cell vacuolation virus
    Mouse polyomavirus
    Bovine polyomavirus
  Genus *Papillomavirus*
    Bovine papillomavirus 1-6
    Canine oral papillomavirus
Family Retroviridae
  Genus "Mammalian type C retroviruses"
    Mammalian type C viruses
      Feline leukemia virus
      Porcine type C virus
  Genus "BLV-HTLV retroviruses"
    Equine leukemia virus=BLV
    Human T lymphotropic virus 1=HTLV-1
    Human T lymphotropic virus 2=HTLV-2
    Simian T lymphotropic virus
  Genus *Lentivirus*
    Equine infectious anemia virus
    Bovine immunodeficiency virus
    Feline immunodeficiency virus
    Caprine arthritis encephalitis virus
    Human immunodeficiency virus 1=HIV-1
    Human immunodeficiency virus 2=HIV-2
    Simian immunodeficiency virus=SIV Further, the method for the detection of the present invention can be applied to any exogenous antigen which can be the cause of a disease of any of humans and mammals other than humans. For example, microorganisms which are zoonotic infectious, specifically, infectious microorganisms toward horse, cattle, sheep, cat, monkey, murine, ostrich or the like are included.

In addition, the method for the detection of the present invention can be suitably applied to exogenous antigens having a property in which the class switching from IgM to IgG necessitates a long period of time. The period of time required for the class switching is not particularly limited, however, for example, 2 months or longer, preferably 3 months or longer, more preferably 1 year or longer is required, and furthermore, it is suitably applied to antigens that complete the class switching within 10 years, preferably within 7 years, more preferably within 4 years. The present inventors verified the appearance of immunoglobulins that executed class switching from IgM to IgG over a period of about one year in response to BDV infection. Currently, antigens that necessitate such a long period of time for class switching have been scarcely identified except for BDV, however, it goes without mentioning that when an antigen having such a property is newly found, the method for the measurement of the present invention can be applied also to such a substance.

(Antigen Polypeptide)

The antigen polypeptide of the present invention, i.e., any one of the antigen polypeptides presented below can be used for diagnosing the infection with BDV. Specifically, an antigen polypeptide described in any of the following 1) to 4) can be used.

1) An antigen polypeptide, which is selected from the p10 region of a BDV protein, characterized in having an ability to detect an anti-BDV antibody by using the polypeptide alone, or in combination with other antigen peptide.

2) An antigen polypeptide characterized in that the selected antigen polypeptide described in the above item 1) has at least 8 amino acids.

3) An antigen polypeptide including the amino acid sequence set out in any one of SEQ ID NOs: 5 to 8.

4) An antigen polypeptide, which is a polypeptide that has an amino acid sequence including deletion, substitution or addition of 1 or several amino acids in the amino acid sequence of an antigen polypeptide described in any one of the above items 1) to 3), having an ability to detect an anti-BDV antibody by using the polypeptide alone, or in combination with other antigen peptide.

The aforementioned antigen polypeptide can be selected one or several kinds thereof. Furthermore, it can be used in combination with other known antigen and/or antigen polypeptide. For example, it can be used in combination with an antigen polypeptide selected from the p24 region and/or p40 region of a BDV protein. Specifically, it can be used in combination with:

1) an antigen polypeptide including an amino acid sequence set out in any one of SEQ ID NOs: 1 to 6; or 2) an antigen polypeptide, which is a polypeptide that has an amino acid sequence including deletion, substitution or addition of 1 or several amino acids in the amino acid sequence described in the above item 1), having an ability to detect an anti-BDV antibody by using the peptide alone, or in combination with other antigen peptide.

In addition, a BDV antibody may be also detected using a polypeptide including one or two or more of any of the amino acid sequences set out in SEQ ID NOs: 5 to 8 in a polypeptide. Moreover, the polypeptide set out in SEQ ID NO: 5, 6, 7 or 8 may be a polypeptide, which has an amino acid sequence including deletion, substitution or addition of 1 or several amino acids in the original sequence thereof.

The antigen polypeptide for use in the present invention can be prepared through the synthesis according to a routine procedure, on the basis of sequence information. Furthermore, one or multiple amino acids can be added to the N-terminus of the antigen polypeptide as a spacer for the purpose of allowing efficient binding of the antigen polypeptide to a solid support, a protein or the like. Although examples of the amino acid which can function as a spacer include glycine and lysine, glycine is preferred.

Examples of the sequence of the BDV antigen polypeptide, which can be specifically illustrated in particular, include the followings. One or two glycine shown in the leftmost part of each sequence represents a spacer.

```
p24
P1:   41-55  GG-QPVDQLLKDLRKNPS       (SEQ ID NO: 1)

P2:   59-77  GG-DPDQRTGREQLSNDELI     (SEQ ID NO: 2)

p40
P3:    3-20  GG-PKRRLVDDADAMEDQDLY    (SEQ ID NO: 3)

P4: 338-358 GG-RYRRREISRGEDGAELSGE   (SEQ ID NO: 4)

p10 (No/98)
P5:   18-36  G-GNTTVESGRLSGGRRRSPD    (SEQ ID NO: 5)

P6:   43-57  G-GLTKTKEDSKECTDP        (SEQ ID NO: 6)

p10 (Con-
trol)
P7:   18-36  G-GNATIESGRLPGGRRRSPD    (SEQ ID NO: 7)

P8:   43-57  G-GVTKTTEDPKECTDP        (SEQ ID NO: 8)
```

(Sample for Detecting Antibody)

The sample for measuring an antibody of the present invention may be any one as long as the antibody in a living body can be measured, which is not particularly limited. However, illustrative examples include whole blood, plasma, serum, bonemarrow, buffycoat, urine, bodyfluid, saliva, nasal drip, lacrimal fluid, substances derived from faeces and the like of a human or an animal.

(Method for Detecting Antibody)

The method for detecting an antibody of the present invention is not particularly limited, but any method can be applied as long as it is a method which can detect immunoglobulin of the IgM class alone, or concurrently detect immunoglobulins of the IgM class and immunoglobulins of the IgG class. In addition, the method for detecting an antibody according to the present invention may be any method in which the antigen polypeptide of the present invention is used, but not particularly limited. For this method, any one of commonly used processes can be applied such as e.g., enzyme immunoassay method, fluorescent immunoassay method, radio immunoassay method, agglutination method, Western blotting method, chemiluminescence immunoassay method and the like. Exemplary particularly preferred method for the detecting includes an immune agglutination method.

For example, measurement by a counting immunoassay method (hereinafter, referred to as "CIA method") which is one type of the agglutination methods can be carried out by the process described in Sysmex Journal Vol. 20 No. 1, 77-86 (1997).

Examples of supports for the sensitization with an antigen peptide include organic polymer powder, inorganic substance powder, microorganisms, hemocytes, cell membrane pieces and the like. Examples of the organic polymer powder which may be illustrated include insoluble agarose, cellulose, insoluble dextran and the like, and preferably, latex particles are widely utilized. Examples of the latex include e.g., polystyrene, polystyrene-styrene sulfonate copolymer, methacrylic polymer, acrylic polymer, acrylonitrile—butadiene styrene copolymer, vinyl chloride—acrylate ester copolymer, polyacetate vinylacrylate and the like.

Any material and particle size of the latex particle for use is allowed as long as the latex particles form an agglutination clump upon the antigen-antibody reaction of the immunoglobulin, without any particular limitation. Mean particle size of the latex is selected ad libitum depending on the detectable concentration of the subject to be measured or on the apparatus for the measurement to be 0.05 to 1.0 μm, preferably 0.3 to 0.85 μm. Examples of the inorganic substance powder which may be illustrated include silica, alumina, or metal as gold, titanium, iron, nickel or the like.

When the support for sensitization with an antigen peptide, specifically the antigen (antibody) binding latex particles, reacts with an antibody (antigen) included in a sample, the latex particles agglutinate depending on the amount of the antibody. In the counting immunoassay, the measurement is executed through conducting discrimination of the difference of the size of each particle thus agglutinated, one by one. For example, when the counted number of the nonagglutinated simple latex particle is referred to as M (Monomer); the counted number of the agglutinated clump involving two or more latex particles is referred to as P (Polymer); and the sum of M and P is referred to as T (Total), degree of the agglutination can be calculated as P/T.

For the sensitization of the antigen to the support, the antigen may be directly sensitized to a latex particle, but any efficient method may be selected such as e.g., sensitization to the latex particle through binding of a ligand such as serum albumin or the like to the intended antigen. The amount of the antigen for the sensitization can be optionally set as needed in the range of up to 100 μg per 1 mg of the support. Preferably, such an amount can be set in the range of up to 100 μg in total of the aforementioned antigen peptide and/or a conjugate BDV antigen peptide in combination with a protein for use as a blocking agent for the purpose of suppressing a nonspecific reaction. The blocking agent can be immobilized on the support after the sensitization of the antigen, or concurrently with antigen.

According to the agglutination method including the CIA method, a reaction between the antigen that is immobilized on a latex particle and the antibody in a specimen sample leads to crosslinking among the latex particles via the antibody to result in the formation of agglutination. In this instance, the crosslinkage can be formed whether the antibody is in the IgM class or the antibody is in the IgG class as long as a reaction with the latex takes place, therefore, concurrent measurement of IgM and IgG is enabled for a specimen sample containing IgM and IgG admixed therewith. In addition, according to the present method, the intended antibody is detected through binding with an insoluble support sensitized with an antigen polypeptide, and thus, an additional reaction of the intended antibody is not required with an antigen, an antibody or the like, which is additionally sensitized with a fluorescent substance or the like. In other words, according to the present method, a BDV antibody can be similarly detected also for samples of a human and a mammal other than humans, without altering the reagent. Because BDV relates to zoonotic infections which can infect mammals such as horses as well as humans, it is advantageous to adopt the CIA method as demonstrated herein.

The method for the detection can be carried out in accordance with a known method through setting the size or concentration of the insoluble support for use, and the reaction time, by measuring the increase or decrease of the intensity of scattering ray, the absorbance or the intensity of transmitted beam. These methods may be used in combination of two or more types thereof.

The present invention is also directed to a kit of the reagent for immunoassay for use in the immunoassay method as described above. Moreover, the present invention is also directed to a reagent including an antigen polypeptide, and a reagent kit.

EXAMPLES

The present invention is specifically explained below with reference to Examples, however, the present invention is not anyhow limited thereto.

Example 1

Detection of Anti-BDV Antibody

In this Example, the presence/absence of the infection with BDV was examined for 17 horses taken care of in Cape Toi, Miyazaki prefecture. The measurement was carried out for the serums collected in 1998.
(Method for Treatment of Equine Plasma)

After the collection of blood with use of heparin, the blood was ice-cooled followed by a treatment within the day to obtain plasma samples.
(Antigen Peptide)

```
p24 (A)  GG-QPVDQLLKDLRKNPS    (SEQ ID NO: 1)
p40 (C)  GG-PKRRLVDDADAMEDQDLY (SEQ ID NO: 3)
p40 (D)  GG-RYRRREISRGEDGAELSGE (SEQ ID NO: 4)
p10 (G)  G-GNATIESGRLPGGRRRSPD  (SEQ ID NO: 7)
p10 (H)  G-GVTKTTEDPKECTDP     (SEQ ID NO: 8)
```

(Sensitization of Antigen Peptide)
1) Antigen peptide p24 (A): conjugated product prepared by adding 300 μg of the peptide and 120 μg of glutaraldehyde respectively onto 24 μl of 5 mg/ml bovine serum albumin (BSA) (equivalent to 120 μg of BSA) and standing the raw peptide so made for 30 minutes at 30° C.;
2) antigen peptide p40 (C): conjugated product prepared by adding 300 μg of the peptide and 120 μg of glutaraldehyde respectively onto 24 μl of 5 mg/ml bovine serum albumin (BSA) (equivalent to 120 μg of BSA) and standing the raw peptide so made for 30 minutes at 30° C.;
3) antigen peptide p40 (D): conjugated product prepared by adding 300 μg of the peptide and 120 μg of glutaraldehyde respectively onto 24 μl of 5 mg/ml bovine serum albumin (BSA) (equivalent to 120 μg of BSA) and standing the raw peptide so made for 30 minutes at 30° C.;
4) antigen peptide p10 (G): conjugated product prepared by adding 300 μg of the peptide and 120 μg of glutaraldehyde respectively onto 24 μl of 5 mg/ml bovine serum albumin (BSA) (equivalent to 120 μg of BSA) and standing the raw peptide so made for 30 minutes at 30° C.;
5) antigen peptide p10 (H): conjugated product prepared by adding 300 μg of the peptide and 120 μg of glutaraldehyde respectively onto 24 μl of 5 mg/ml bovine serum albumin (BSA) (equivalent to 120 μg of BSA) and standing the raw peptide so made for 30 minutes at 30° C.
Whole amount of each BDV antigen conjugate as described in each of the above 1) to 5) was added to 1 mL of a latex particle suspension (containing 5 mg of latex support having the particle size of 0.8 μm), and left to stand still at 37° C. for 1 hour. Thereafter, the latex particles were washed to preparer the sensitized latex liquid of each antigen. Further, 120 μg of bovine serum albumin (BSA) was similarly added to 1 mL of a latex particle suspension (containing 5 mg of latex support having the particle size of 0.8 μm), and left to stand still at 37° C. for 1 hour. Thereafter, the latex particles were washed to prepare the unsensitized latex liquid.
(Detection)

Anti-BDV antibody was detected using a measuring equipment manufactured by Sysmex Corporation (PAMIA-50).

Onto wells of a reaction plate were added 80 μL of a buffer for the latex agglutination reaction, 10 μL of each equine serum sample and 10 μL of a solution containing the latex particles prepared as described above, followed by a reaction at 45° C.

After about 15 minutes elapsed following initiation of the reaction, 19 μL of the reaction mixture was added to 950 μL of Sheath fluid in the chamber of the equipment to dilute 51 times. The agglutination reaction was terminated by the dilution, and thereafter, degree of the agglutination was detected at the optical detection element.

With the use of a calibration curve which had been previously provided by the measurement (negative control P/T % and cut off control P/T %), the cut off index (COI) value of the specimen was determiner according to the formula 1. Determination was conducted as described below in accordance with the COI value of the specimen.

positive: $COI \geq 1$
Negative: $COI < 1$ $$\text{Cut Off Index } (COI) = \frac{(P/T \text{ \%, measured value of the specimen} - P/T \text{ \% when unsensitized latex particles were used})}{(\text{Cut off control } P/T \text{ \%} - \text{Negative control } P/T \text{ \%})} \quad \text{Formula 1}$$

(Results of Detection)

Results of the detection described above are presented in Table 1. Consequently, BDV positive was exhibited for all of the equine serums.

Comparative Example 1

Measurement was carried out for serums collected in 1998 of the 17 horses described in Example 1, using an ECLIA method explained below as a conventional method. Process for the treatment of the equine serum was carried out similarly to that described in Example 1.
1. Measurement Principle:
ECLIA method is based on a sandwich method in principle, in which micro beads bound with a BDV antigen as a solid phase and an anti-human IgG monoclonal antibody labeled with a Ru complex that emits light upon electrochemical alteration are employed.
Each reaction is explained below.
First Reaction
Upon reaction between the antigen-bound beads and the specimen, antibodies in the specimen are bound to the antigens on the beads.
Second Reaction
The antibodies bound on the beads are subjected to a reaction with a ruthenium labeled anti-human IgG monoclonal antibody to allow binding in a sandwiching manner.

Third Reaction

When the beads are collected on an electrode and an electric energy is imparted thereto, the Ru complex emits light depending on the amount of the ruthenium labeled anti-IgG monoclonal antibody that was bound on the beads via the antibody. The antibody in the specimen is detected by measuring the amount of this emitted light.

2. Method of Detection:

Detection was performed in accordance with the following procedures.

(1) To a reaction tube were injected a reaction fluid 200 μL, a subject specimen 20 μL, and an antigen bound beads fluid 25 μL, and then the reaction was allowed at 30° C. for 9 minutes. (First reaction)

(2) A magnet was brought close to the reaction tube to collect the beads on the wall of the reaction tube. Thereafter, the fluid in the reaction tube was aspirated to eliminate, and a washing fluid was further injected followed by stirring with shaking.

(3) A magnet was brought close to the reaction tube to collect the beads on the wall of the reaction tube. Thereafter, the fluid in the reaction tube was eliminated.

(4) To the reaction tube was injected 200 μL of a ruthenium labeled anti-IgG monoclonal antibody fluid, and the reaction was allowed at 30° C. for 9 minutes. (Second reaction)

(5) A magnet was brought close to the reaction tube to collect the beads on the wall of the reaction tube. Thereafter, the fluid in the reaction tube was eliminated, and a washing fluid was further injected followed by stirring with shaking.

(6) A magnet was brought close to the reaction tube to collect the beads on the wall of the reaction tube. Thereafter, the fluid in the reaction tube was eliminated, and 300 μL of a luminescent electrolyte was injected thereto. The beads were lead to a flow cell electrode to measure the amount of the emitted light. (Third reaction) Then, determination was conducted as positive for equal to or greater than 1000, and as negative for less than 1000.

3. Antigens Used

The following two kinds of antigens were used:
BDV p24 recombinant antigen; and
BDV p40 recombinant antigen.

4. Results

As a result, with respect to the specimens No. 1 to 23, all exhibited negative results according to the conventional method, whilst positive results were shown for any of 5 kinds of the antigen polypeptides according to the embodiment method, when the results of the samples obtained in 1998 are compared (Table 1).

On the other hand, with respect to the specimens No. 24 to 36, both results of the detection according to the conventional method and according to the embodiment method were positive, which indicated the consistency (Table 2). Moreover, with respect to the specimens No. 37 to 47, both results of the detection according to the conventional method and according to the embodiment method were negative, which indicated the consistency (Table 3).

In respect of the specimens that indicated inconsistency, positive determination was effected in the system in which the detection was carried out using the antigen polypeptide of the embodiment method invention, despite of negative results according to the conventional method, thereby enabling the detection of a BDV antibody with favorable sensitivity. In regard to specimens No. 11, 12, 14, 15 and 18, the BDV antibody could be detected only with p10 (H). Accordingly, the combination of multiple antigen polypeptides enables elevating the detection ability of an anti-BDV antibody.

TABLE 1

| Number of Specimen | Embodiment method (unit: C. O. I.) in 1998 | | | | | Conventional method Positive: 1000 or greater in 1998 |
| --- | --- | --- | --- | --- | --- | --- |
| | P24 A: 41–55 | P40 C: 3–20 | P40 D: 338–358 | P10(G) G: 18–36 | P10(H) H: 43–57 | |
| 1 | 2.5 (+) | 1.58 (+) | 0.00 | 0.76 | 4.38 (+) | 228 |
| 2 | 1.3 (+) | 1.02 (+) | 0.26 | 1.4 (+) | 4.14 (+) | 588 |
| 3 | 24.62 (+) | 12.66 (+) | 1.62 (+) | 10.1 (+) | 6.78 (+) | 634 |
| 4 | 60.44 (+) | 29.7 (+) | 1.74 (+) | 9.81 (+) | 4.78 (+) | 361 |
| 5 | 5.12 (+) | 4.7 (+) | 2.36 (+) | 7.12 (+) | 6.18 (+) | 397 |
| 6 | 2.88 (+) | 1.14 (+) | 0.02 | 1.140 (+) | 0.36 | 276 |
| 7 | 1.46 (+) | 3.24 (+) | 0.64 | 1.02 (+) | 0.60 | 276 |
| 8 | 11.56 (+) | 6.48 (+) | 0.56 | 5.33 (+) | 2.84 (+) | 116 |
| 9 | 89.46 (+) | 54.76 (+) | 13.84 (+) | 76.42 (+) | 54.64 (+) | 31 |
| 10 | 0.50 | 1.10 (+) | 0.00 | 0.00 | 0.11 | 623 |
| 11 | 0.16 | 0.32 | 0.02 | 0.00 | 1.76 (+) | 350 |
| 12 | 0.94 | 0.46 | 0.00 | 0.08 | 113.44 (+) | 349 |
| 13 | 2.98 (+) | 0.00 | 0.00 | 0.02 | 0.00 | 348 |
| 14 | 0.70 | 0.02 | 0.00 | 0.20 | 1.86 (+) | 286 |
| 15 | 0.14 | 0.32 | 0.18 | 22.88 (+) | 1.14 (+) | 272 |

TABLE 1-continued

| Number of Specimen | Embodiment method (unit: C. O. I.) in 1998 | | | | | Conventional method Positive: 1000 or greater in 1998 |
|---|---|---|---|---|---|---|
| | P24 A: 41–55 | P40 C: 3–20 | P40 D: 338–358 | P10(G) G: 18–36 | P10(H) H: 43–57 | |
| 16 | 1.08 (+) | 2.50 (+) | 0.00 | 0.10 | 0.00 | 243 |
| 17 | 1.86 (+) | 0.92 | 0.30 | 1.34 (+) | 0.58 | 230 |
| 18 | 0.00 | 0.76 | 0.00 | 0.82 | 4.18 (+) | 201 |
| 19 | 0.00 | 0.42 | 24.92 (+) | 0.26 | 2.52 (+) | 173 |
| 20 | 0.06 | 0.40 | 3.14 (+) | 0.00 | 0.00 | 108 |
| 21 | 0.14 | 3.44 (+) | 0.44 | 0.18 | 0.18 | 79 |
| 22 | 0.88 | 3.72 (+) | 0.34 | 0.38 | 0.00 | 75 |
| 23 | 2.12 (+) | 0.08 | 0.24 | 0.48 | 0.62 | 48 |

TABLE 2

| Number of Specimen | Embodiment method (unit: C. O. I.) in 1998 | | | | | Conventional method Positive: 1000 or greater in 1998 |
|---|---|---|---|---|---|---|
| | P24 A: 41–55 | P40 C: 3–20 | P40 D: 338–358 | P10(G) G: 18–36 | P10(H) H: 43–57 | |
| 24 | 0.64 | 3.4 (+) | 3.44 (+) | 9.11 (+) | 73.92 (+) | 9124 (+) |
| 25 | 14.66 (+) | 14.38 (+) | 8.92 (+) | 13.30 (+) | 12.06 (+) | 19648 (+) |
| 26 | 4.02 (+) | 1.64 (+) | 2.44 (+) | 4.89 (+) | 4.08 (+) | 14710 (+) |
| 27 | 1.46 (+) | 2.8 (+) | 1.66 (+) | 0.46 | 0.00 | 9614 (+) |
| 28 | 12.14 (+) | 2.56 (+) | 0.28 | 1.30 (+) | 3.64 (+) | 5960 (+) |
| 29 | 1.86 (+) | 1.62 (+) | 0.40 | 1.64 (+) | 7.02 (+) | 2689 (+) |
| 30 | 1.1 (+) | 1.38 (+) | 0.58 | 1.50 (+) | 1.58 (+) | 1365 (+) |
| 31 | 9.36 (+) | 6.7 (+) | 0.00 | 2.16 (+) | 0.10 | 1935 (+) |
| 32 | 0.18 | 0.24 | 28.24 (+) | 0.68 | 33.84 (+) | 1642 (+) |
| 33 | 0.12 | 0.04 | 0.00 | 0.24 | 7.24 (+) | 2930 (+) |
| 34 | 2.78 (+) | 1.38 (+) | 0.46 | 0.60 | 0.32 | 1813 (+) |
| 35 | 4.84 (+) | 0.74 | 0.22 | 1.16 (+) | 0.76 | 1799 (+) |
| 36 | 0.42 | 3.62 (+) | 23.42 (+) | 0.00 | 0.00 | 1703 (+) |

TABLE 3

| Number of Specimen | Embodiment method (unit: C. O. I.) in 1998 | | | | | Conventional method Positive: 1000 or greater in 1998 |
|---|---|---|---|---|---|---|
| | P24 A: 41–55 | P40 C: 3–20 | P40 D: 338–358 | P10(G) G: 18–36 | P10(H) H: 43–57 | |
| 37 | 0.00 | 0.00 | 0.00 | 0.00 | 0.00 | 407 |
| 38 | 0.56 | 0.22 | 0.16 | 0.00 | 0.00 | 103 |
| 39 | 0.58 | 0.34 | 0.20 | 0.64 | 0.14 | 165 |

TABLE 3-continued

| Number of Specimen | Embodiment method (unit: C. O. I.) in 1998 | | | | | Conventional method Positive: 1000 or greater in 1998 |
|---|---|---|---|---|---|---|
| | P24 A: 41–55 | P40 C: 3–20 | P40 D: 338–358 | P10(G) G: 18–36 | P10(H) H: 43–57 | |
| 40 | 0.12 | 0.24 | 0.00 | 0.00 | 0.00 | 449 |
| 41 | 0.00 | 0.00 | 0.00 | 0.00 | 0.00 | 373 |
| 42 | 0.04 | 0.06 | 0.00 | 0.12 | 0.00 | 76 |
| 43 | 0.00 | 0.08 | 0.00 | 0.00 | 0.00 | 443 |
| 44 | 0.02 | 0.00 | 0.52 | 0.00 | 0.00 | 138 |
| 45 | 0.00 | 0.72 | 0.32 | 0.00 | 0.00 | 276 |
| 46 | 0.62 | 0.80 | 0.08 | 0.28 | 0.00 | 263 |
| 47 | 0.54 | 0.00 | 0.00 | 0.12 | 0.00 | 352 |

Experimental Example 1

Ratio of IgM and IgG in the detected antibodies was determined for specimens No. 5 and 6 which indicated inconsistent results of the detection according to the conventional method and to the embodiment method, as well as specimens No. 25 and 26 which indicated consistent results of the detection.

Anti-equine IgM goat serum (COSMO BIO Co., Ltd.) and anti-equine IgG goat serum (COSMO BIO Co., Ltd.) stock solutions were employed as the reagent for absorption. A mixture of a buffer and an anti-equine IgM serum at a ratio of 9:1 was used as an IgM absorption buffer, and similarly, a mixture of a buffer and an anti-equine IgG serum at a ratio of 9:1 was used as an IgG absorption buffer.

Measurement of P/T % was carried out for the IgM absorption buffer and the IgG absorption buffer with PAMIA-50 in a similar manner to that described in Example 1. Rate of IgM absorption and rate of IgG absorption were determined in accordance with the formula 2.

$$\text{Rate of } IgM \text{ absorption} = \frac{(COI \text{ of the specimen}) - (COI \text{ in the } IgM \text{ absorption buffer})}{COI \text{ of the specimen}} \times 100\% \quad \text{[Formula 2]}$$

$$\text{Rate of } IgG \text{ absorption} = \frac{(COI \text{ of the specimen}) - (COI \text{ in the } IgG \text{ absorption buffer})}{COI \text{ of the specimen}} \times 100\%$$

Figure 2:
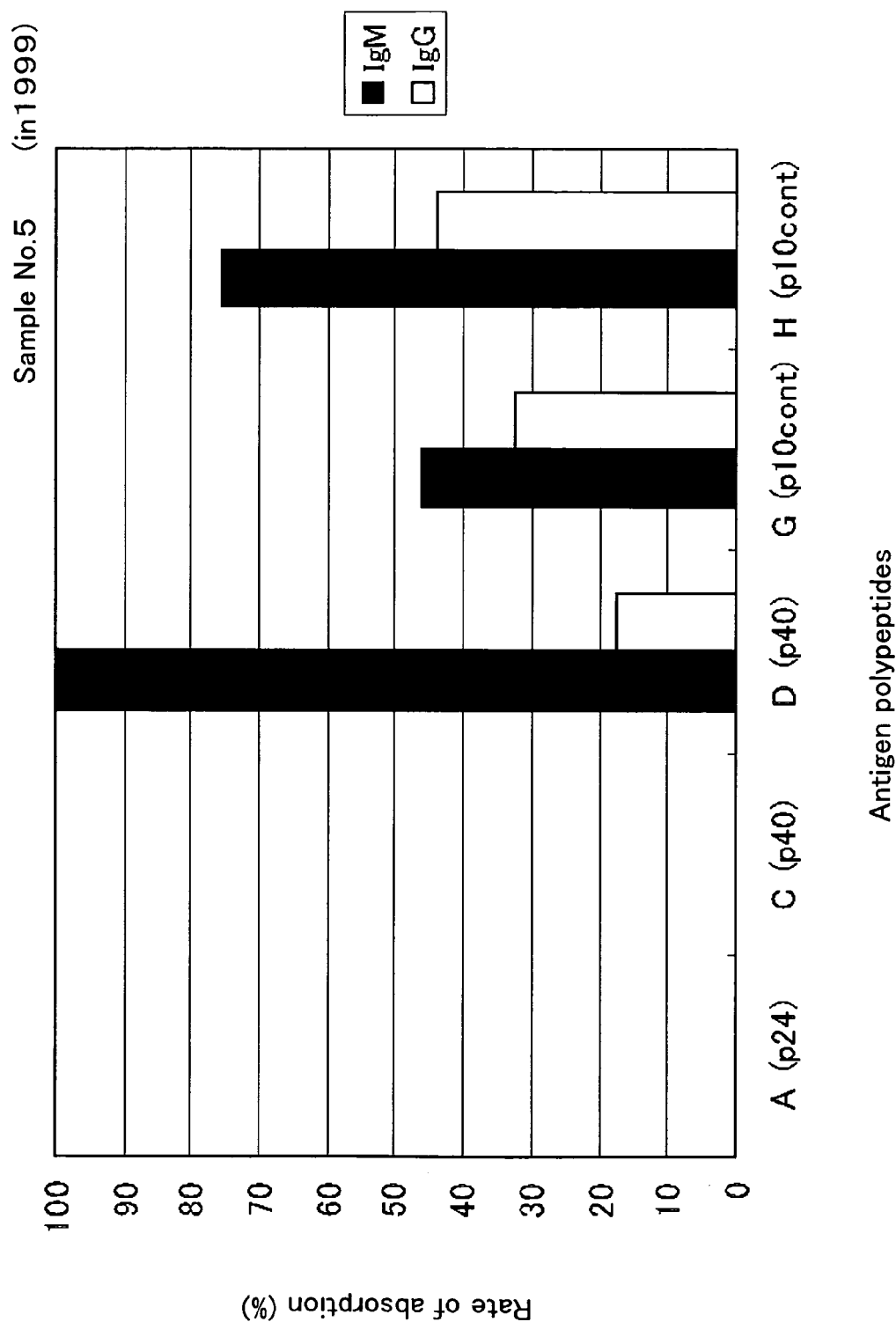
FIG. 2 A drawing showing results of the detection of a sample collected in 1999 of specimen No. 5 (Experimental Example 1).
Figure 3:
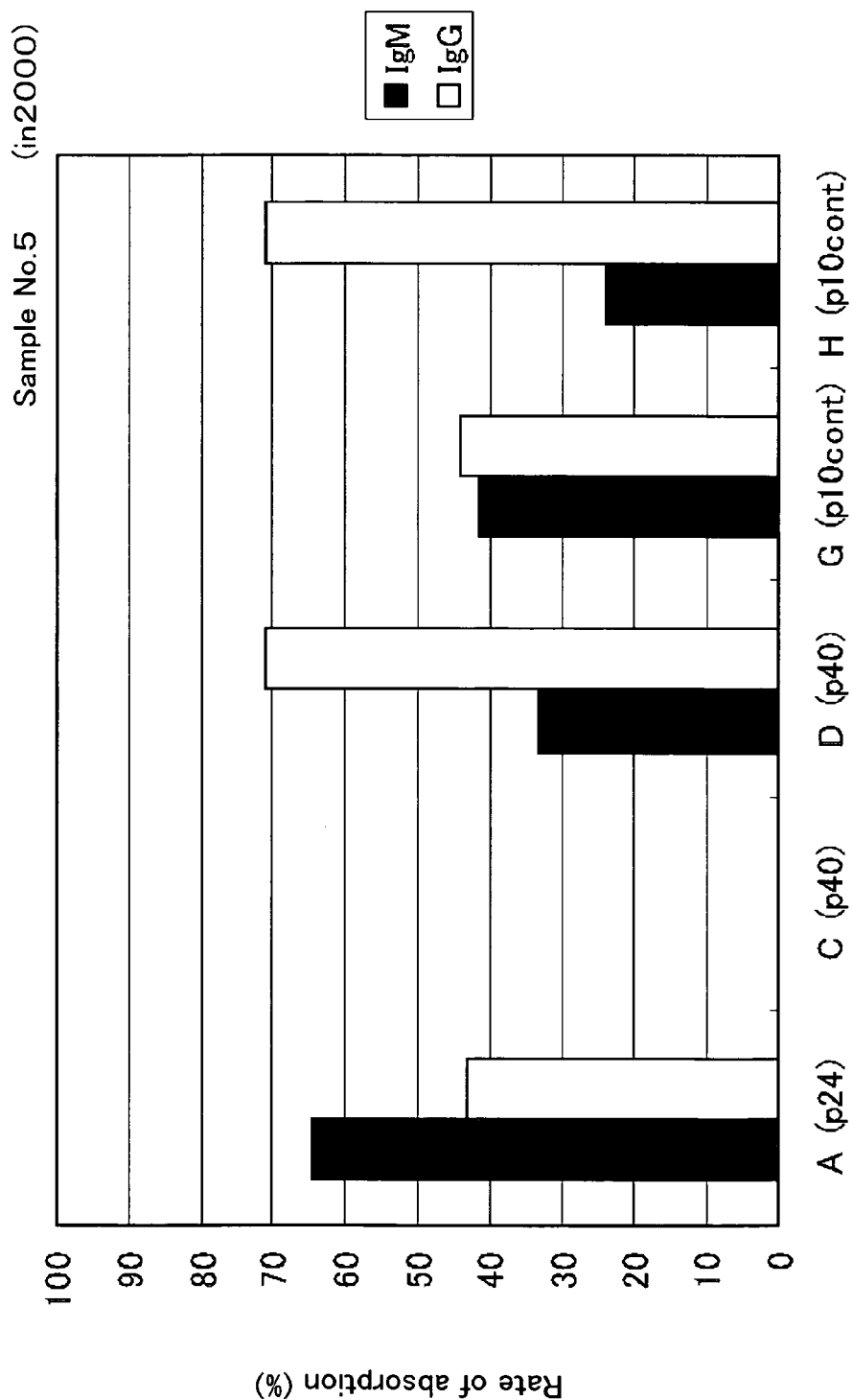
FIG. 3 A drawing showing results of the detection of a sample collected in 2001 of specimen No. 5 (Experimental Example 1).
Figure 4:
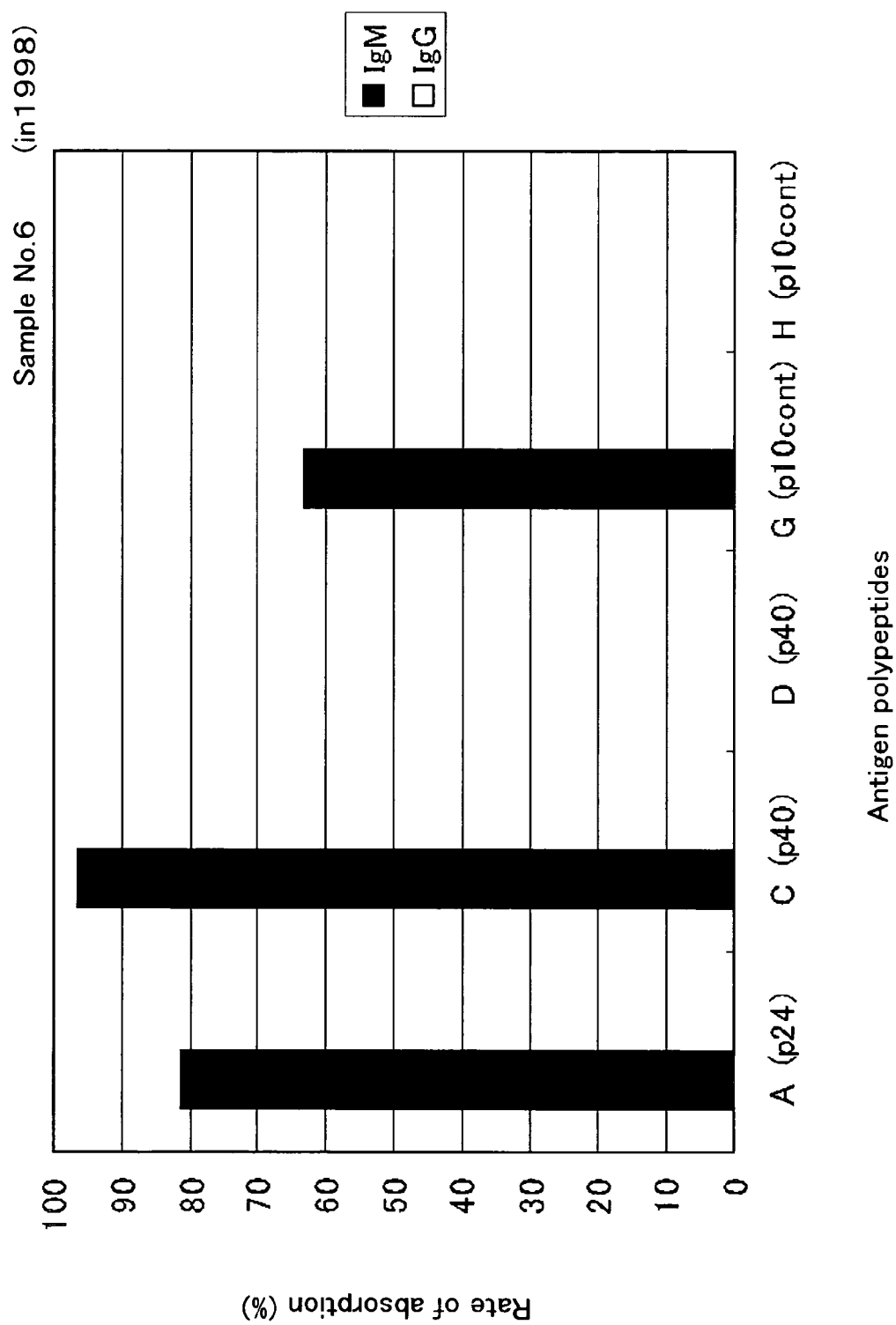
FIG. 4 A drawing showing results of the detection of a sample collected in 1998 of specimen No. 6 (Experimental Example 1).
Figure 5:
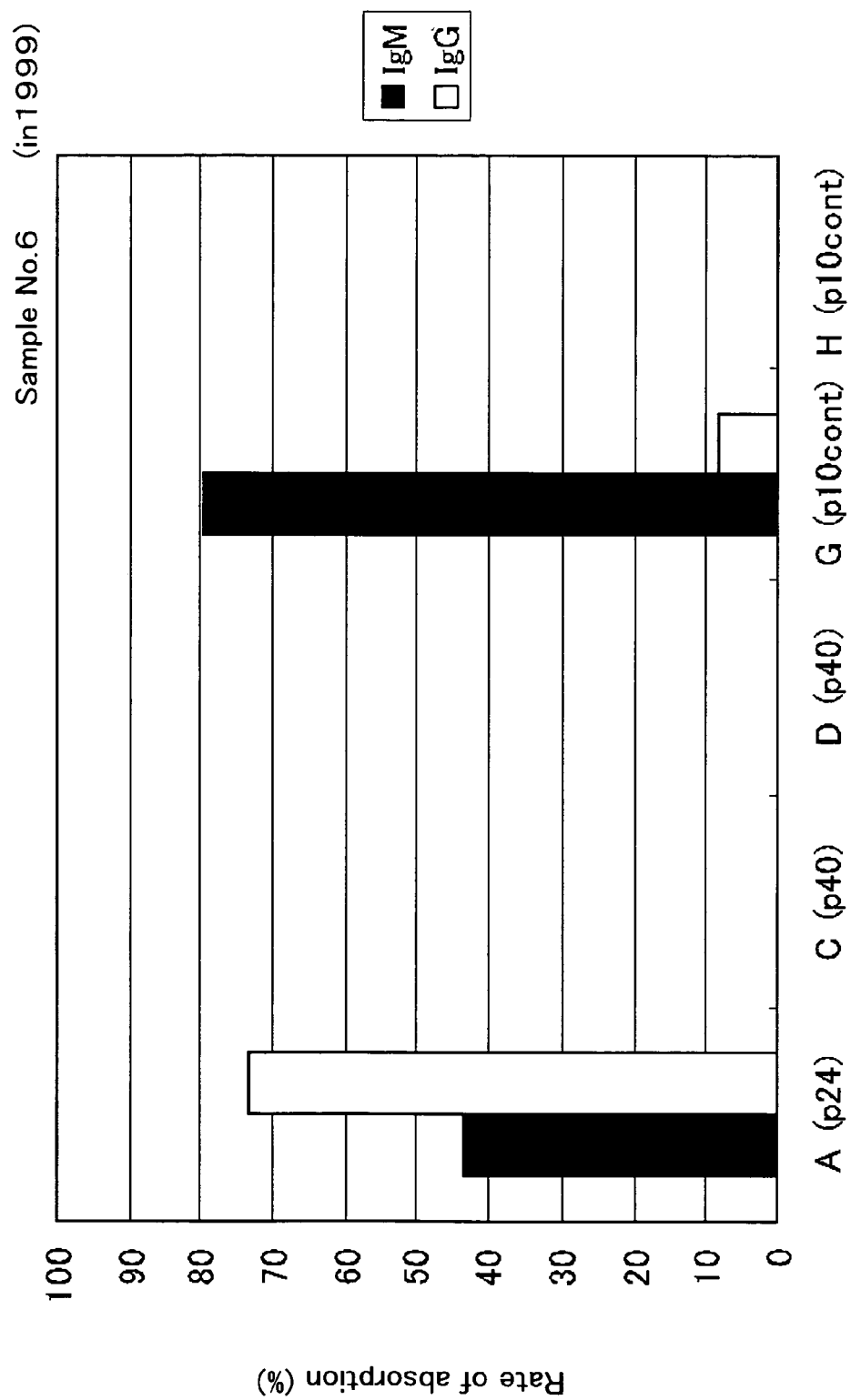
FIG. 5 A drawing showing results of the detection of a sample collected in 1999 of specimen No. 6 (Experimental Example 1).
Figure 6:
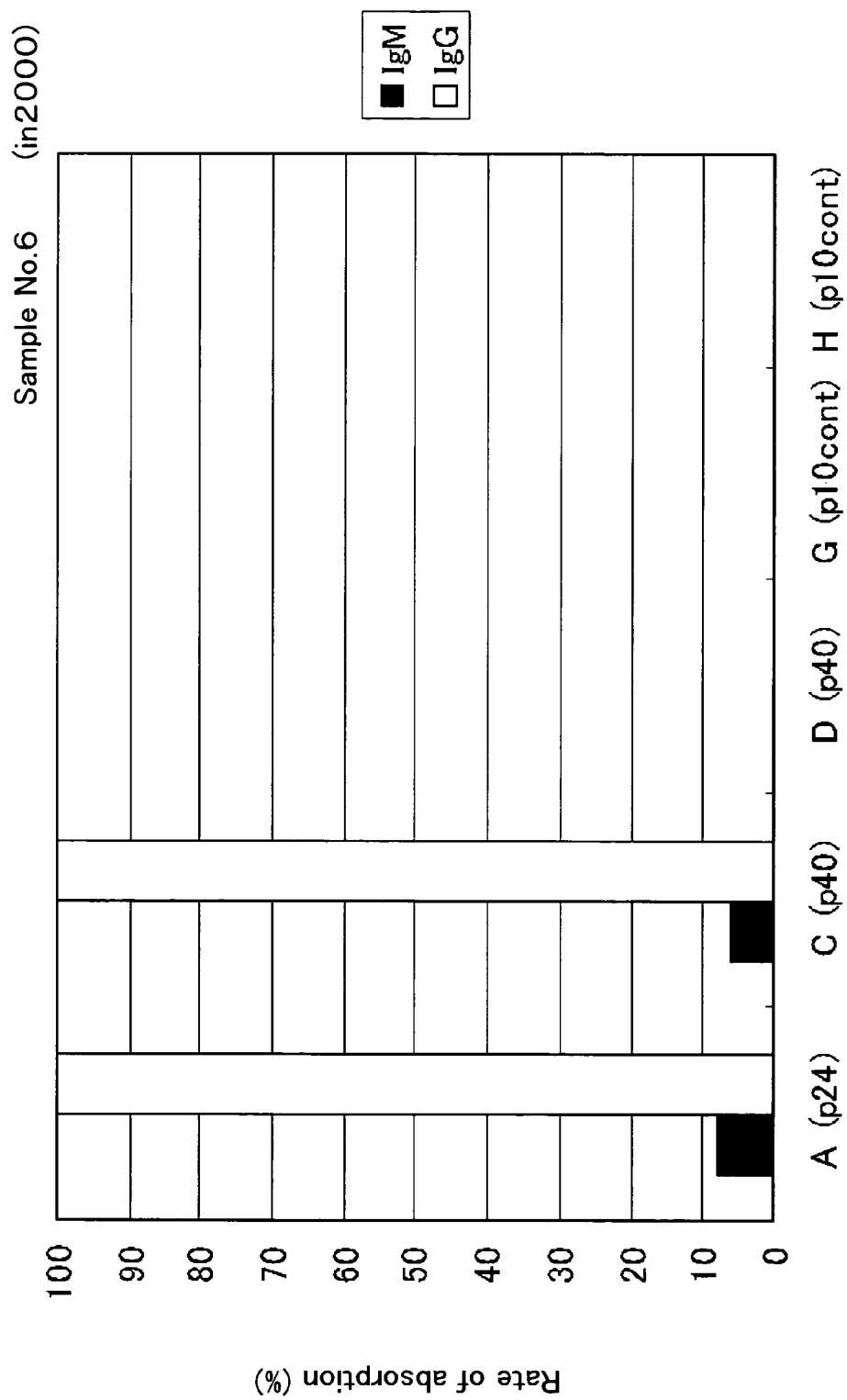
FIG. 6 A drawing showing results of the detection of a sample collected in 2000 of specimen No. 6 (Experimental Example 1).
Figure 7:
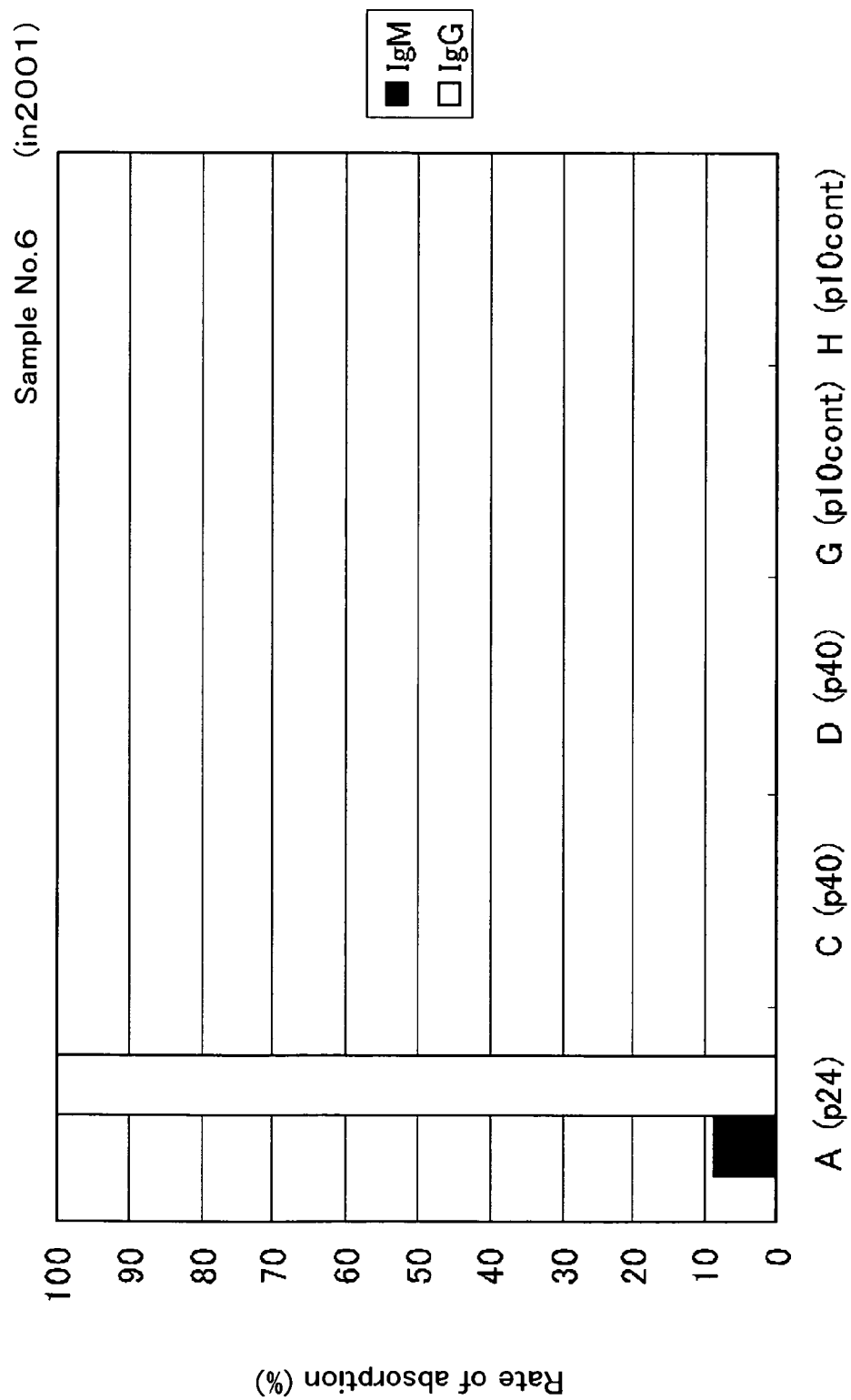
FIG. 7 A drawing showing results of the detection of a sample collected in 2001 of specimen No. 6 (Experimental Example 1).
Figure 8:
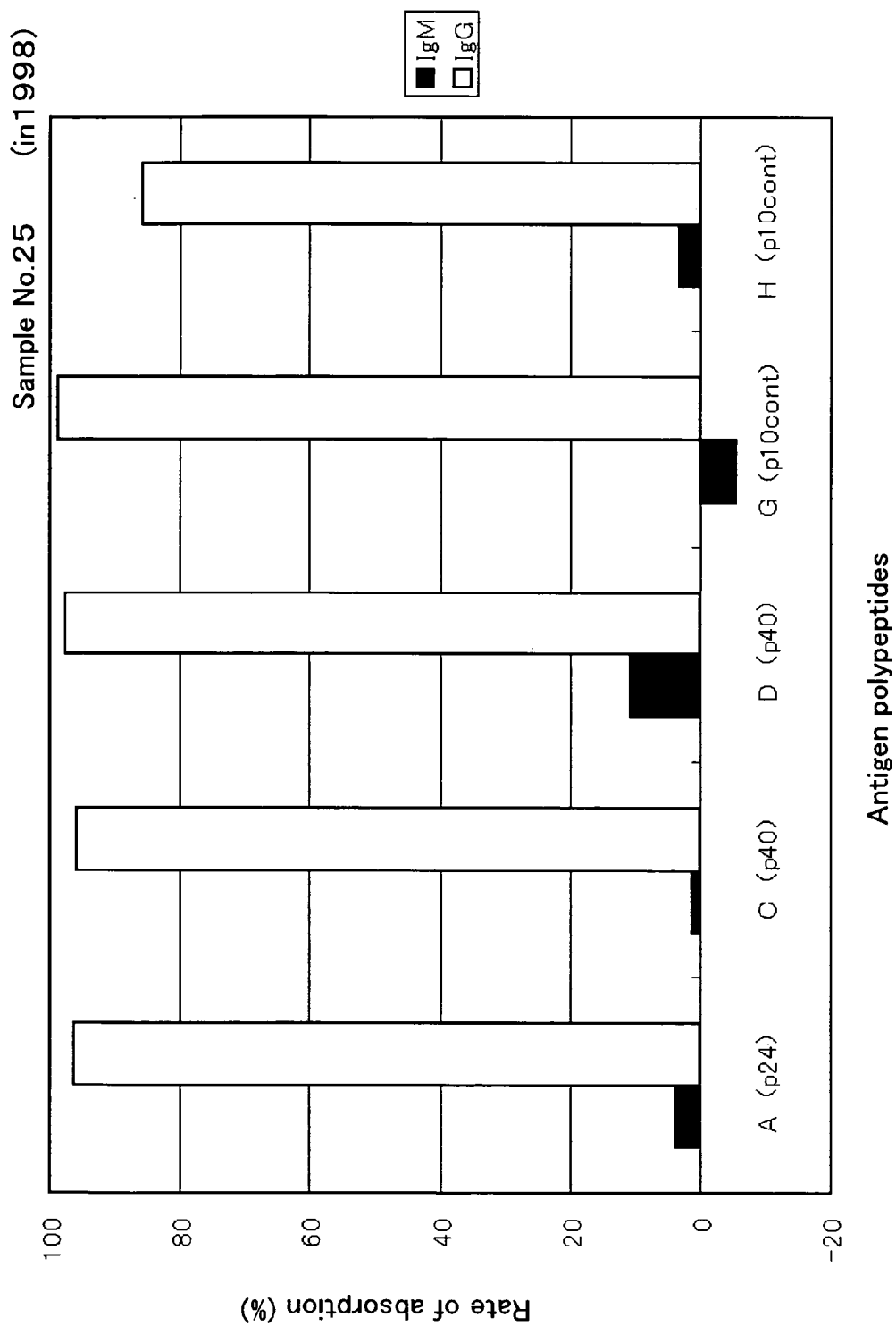
FIG. 8 A drawing showing results of the detection of a sample collected in 1998 of specimen No. 25 (Experimental Example 1).
Figure 9:
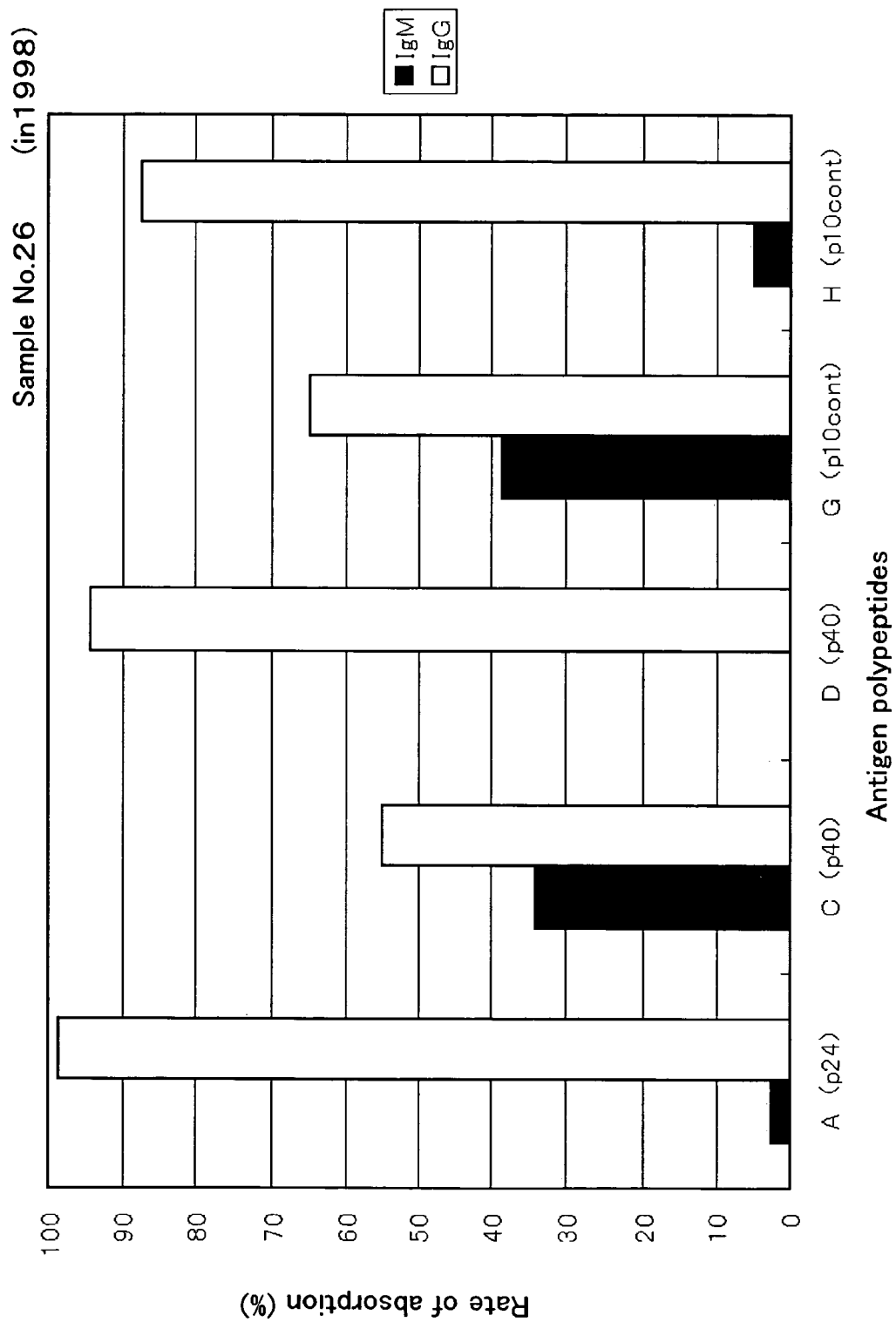
FIG. 9 A drawing showing results of the detection of a sample collected in 1998 of specimen No. 26 (Experimental Example 1).

Results of the detection of serums collected in 1998, 1999 and 2001 of the specimen No. 5 are shown in FIGS. 1 to 3, respectively; results of the detection of serums collected in 1998 to 2001 of the specimen No. 6 are shown in FIGS. 4 to 7, respectively; results of the detection of serum collected in 1998 of the specimen No. 25 are shown in FIG. 8; and results of the detection of a serum collected in 1998 of the specimen No. 26 are shown in FIG. 9.

Consequently, with respect to specimens No. 5 and No. 6 with difference found among the results of the detection according to the conventional method and the present method for the detection, the more appearance of IgM was found than the appearance of IgG in serum samples collected in 1998 and 1999, while no appearance of IgG was found in a serum sample collected in 2001. On the other hand, with respect to specimens No. 25 and No. 26 with no difference found among the results of the detection according to the conventional method and the embodiment method, the more appearance of IgG was found than the appearance of IgM in a serum sample collected in 1998.

From these results of experiment, it was revealed that a long period of time was required for the class switching from IgM to IgG following the infection with BDV, with respect to specimens 5 and 6.

Example 2

For 82 horses taken care of in Cape Toi, Miyazaki prefecture, survival rate in 5 years was studied for the group determined as being BDV antibody-positive and negative using the antigen polypeptide of the embodiment method according to each method for the detection, i.e., as a result of the detection according to the method described in Examples 1, and as a result of the detection according to the method of Comparative Example that is a conventional method of a serum collected in 1998. Consequently, as shown in Table 4, mortality rate in the instance of antibody positive was 66.7%, whilst mortality rate in the instance of antibody negative was 28.3%, when the detection was carried out according to the embodiment method. On the other hand, when the detection was carried out according to the conventional method, mortality rate in the instance of antibody positive was 52.4%, however, mortality rate of 42.6% was presented even in the instance of antibody negative. When the measurement was carried out using the antigen polypeptide of the present invention, high mortality rate was exhibited in the instance of antibody positive, thus, the results of the measurement reflected the mortality rate. Therefore, to conduct more accurate examination of BDV infection was permitted.

TABLE 4

Follow up of BDV antibody positive horses

| | | 1998 | 2002 |
|---|---|---|---|
| Agglutination method | Positive | 36 | 12(33.3%) confirmed as alive |
| | | | 7(19.4%) confirmed as dead |

TABLE 4-continued

Follow up of BDV antibody positive horses

| | | 1998 | 2002 | |
|---|---|---|---|---|
| (Embodiment method) | | | 17(47.2%) uncertain | death + uncertain = 24(66.7%) |
| Agglutination method | Negative | 46 | 33(71.7%) confirmed as alive<br>4(8.7%) confirmed as dead | |
| (Embodiment method) | | | 9(19.6%) Uncertain | death + uncertain = 13(28.3%) |
| Conventional method | Positive | 21 | 10(47.6%) Confirmed as alive<br>5(23.8%) confirmed as dead<br>6(28.6%) uncertain | death + uncertain = 11(52.4%) |
| Conventional method | Negative | 61 | 35(57.4%) confirmed as alive<br>6(9.8%) confirmed as dead<br>20(32.8%) uncertain | death + uncertain = 26(42.6%) |

INDUSTRIAL APPLICABILITY

According to the method for the detection in which the antigen polypeptide of the present invention is used, a sample, which had not been able to be detected when the measurement according to the conventional method was carried out, could be also determined as BDV positive, as a result of the concurrent measurement of IgM and IgG for BDV. The present invention enables the determination of the presence/absence of an infection through detecting the appearance of IgM without overlooking, also in instances of exogenous antigens such as BDV, which necessitate a long period of time for the class switching from IgM to IgG of the immunoglobulins, where the antigen itself can not be detected owing to the slight amount of the antigen.

Additionally, the demonstrated CIA method herein is extremely useful as a method of examining BDV, because BDV which may be the cause of zoonotic infections can be detected using the identical reagent for horses, humans and the like.

What is claimed is:

1. A method for determining whether a subject has been infected with Borna disease virus (BDV), comprising:
   (a) providing a support having immobilized thereon p10 BDV synthetic antigen polypeptide and p24 BDV synthetic antigen polypeptide;
   (b) reacting the resulting support with a sample from a living body; and
   (c) assaying for both anti-BDV IgM antibody and anti-BDV IgG antibody which bind to said p10 BDV synthetic antigen polypeptide and said p24 BDV synthetic antigen polypeptide immobilized on said support, so as to detect said anti-BDV IgM antibody and/or anti-BDV IgG antibody in said sample, wherein said subject is determined to have been infected with BDV when said anti-BDV IgM antibody or said anti-BDV IgG antibody, or both said anti-BDV IgM antibody and said anti-BDV IgG antibody is detected,
   wherein the p10 BDV synthetic antigen polypeptide has an amino acid sequence as set forth in SEQ ID NO: 8,
   wherein the p24 BDV synthetic antigen polypeptide has an amino acid sequence as set forth in SEQ ID NO: 1.

2. A method for determining whether a subject has been infected with Borna disease virus (BDV), comprising:
   (a) providing a support having immobilized thereon p10 BDV synthetic antigen polypeptide and p40 BDV synthetic antigen polypeptide;
   (b) reacting the resulting support with a sample from a living body; and
   (c) assaying for both anti-BDV IgM antibody and anti-BDV IgG antibody which bind to said p10 BDV synthetic antigen polypeptide and said p40 BDV synthetic antigen polypeptide immobilized on said support, so as to detect said anti-BDV IgM antibody and/or anti-BDV IgG antibody in said sample, wherein said subject is determined to have been infected with BDV when the said anti-BDV IgM antibody or the said anti-BDV IgG antibody, or both the said anti-BDV IgM antibody and the said anti-BDV IgG antibody is detected, wherein the p10 BDV synthetic antigen polypeptide has an amino acid sequence as set forth in SEQ ID NO: 8, wherein the p40 BDV synthetic antigen polypeptide has an amino acid sequence as set forth in SEQ ID NO: 3.

3. A method for determining whether a subject has been infected with Borna disease virus (BDV), comprising:
(a) providing a support having immobilized thereon p10 BDV synthetic antigen polypeptide, p24 BDV synthetic antigen polypeptide and p40 BDV synthetic antigen polypeptide;
(b) reacting the resulting support with a sample from a living body; and
(c) assaying for both anti-BDV IgM antibody and anti-BDV IgG antibody which bind to said p10 BDV synthetic antigen polypeptide, said p24 BDV synthetic antigen polypeptide and said p40 BDV synthetic antigen polypeptide immobilized on said support, so as to detect said anti-BDV IgM antibody and/or anti-BDV IgG antibody in said sample, wherein said subject is determined to have been infected with BDV infection is detected in said subject when the said anti-BDV IgM antibody or the said anti-BDV IgG antibody, or both the said anti-BDV IgM and the said anti-BDV IgG antibody is detected, wherein the p10 BDV synthetic antigen polypeptide has an amino acid sequence as set forth in SEQ ID NO: 8, wherein the p24 BDV synthetic antigen polypeptide has an amino acid sequence as set forth in SEQ ID NO: 1, wherein the p40 BDV synthetic antigen polypeptide has an amino acid sequence as set forth in SEQ ID NO: 3.

* * * * *